United States Patent [19]

Kumar et al.

[11] Patent Number: 4,668,589
[45] Date of Patent: May 26, 1987

[54] AMINOPHENOXYCYCLOTRIPHOSPHA-ZENE CURED EPOXY RESINS AND THE COMPOSITES, LAMINATES, ADHESIVES AND STRUCTURES THEREOF

[75] Inventors: Devendra Kumar, Kanpur, India; George M. Fohlen, Millbrae; John A. Parker, Los Altos, both of Calif.

[73] Assignee: The United States of America as represented by the Administrator of the National Aeronautics and Space Administration, Washington, D.C.

[21] Appl. No.: 806,572

[22] Filed: Nov. 21, 1985

[51] Int. Cl.$^4$ ............................................. C08G 79/02
[52] U.S. Cl. .................................... 428/417; 428/413; 528/108; 528/168
[58] Field of Search ............... 528/108, 168; 428/413, 428/417; 523/452

[56] References Cited

U.S. PATENT DOCUMENTS

| | | | |
|---|---|---|---|
| 3,867,344 | 2/1975 | Frank et al. | 528/108 |
| 3,933,738 | 1/1976 | Munch et al. | 523/452 |
| 4,061,606 | 12/1977 | Dieck et al. | 528/168 |
| 4,107,146 | 8/1978 | Dieck et al. | 528/168 |
| 4,124,557 | 11/1978 | Dieck et al. | 528/399 |
| 4,316,006 | 2/1982 | McEwen | 528/108 |
| 4,405,738 | 9/1983 | McNeely | 528/399 |

Primary Examiner—Veronica P. Hoke
Attorney, Agent, or Firm—Darrell G. Brekke; John R. Manning; Robert D. Marchant

[57] ABSTRACT

Aminophenoxycyclotriphosphazenes such as hexakis(4-aminophenoxy)cyclotriphosphazene and tris(4-aminophenoxy)-tris phenoxyclyclotriphosphazene are used as curing agents for epoxy resins. These 1,2-epoxy resins are selected from di- or polyepoxide-containing organic moieties of the formula $(CH_2—CHO—CH_2)_m—W—R—W—(CH_2CH—CH_2O)_m$ where R is diphenyldimethylmethane, diphenylmethane, bis(dibromophenyl)dimethylmethane, or

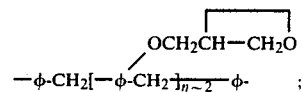

W is a nitrogen or oxygen atom; and m is 1 when W is oxygen and 2 when W is nitrogen. The resins are cured thermally in stages at between about 110° to 135° C. for between about 1 and 10 min, then at between about 175° to 185° C. for between about 0.5 to 10 hr and post-cured at between about 215° and 235° C. for between abut 0.1 and 2 hr. These resins are useful for making fire-resistant elevated temperature stable composites, laminates (e.g. graphite fiber or fiberglass), molded parts, and adhesives and structures, usually for aircraft secondary structures and for spacecraft construction.

20 Claims, 2 Drawing Figures

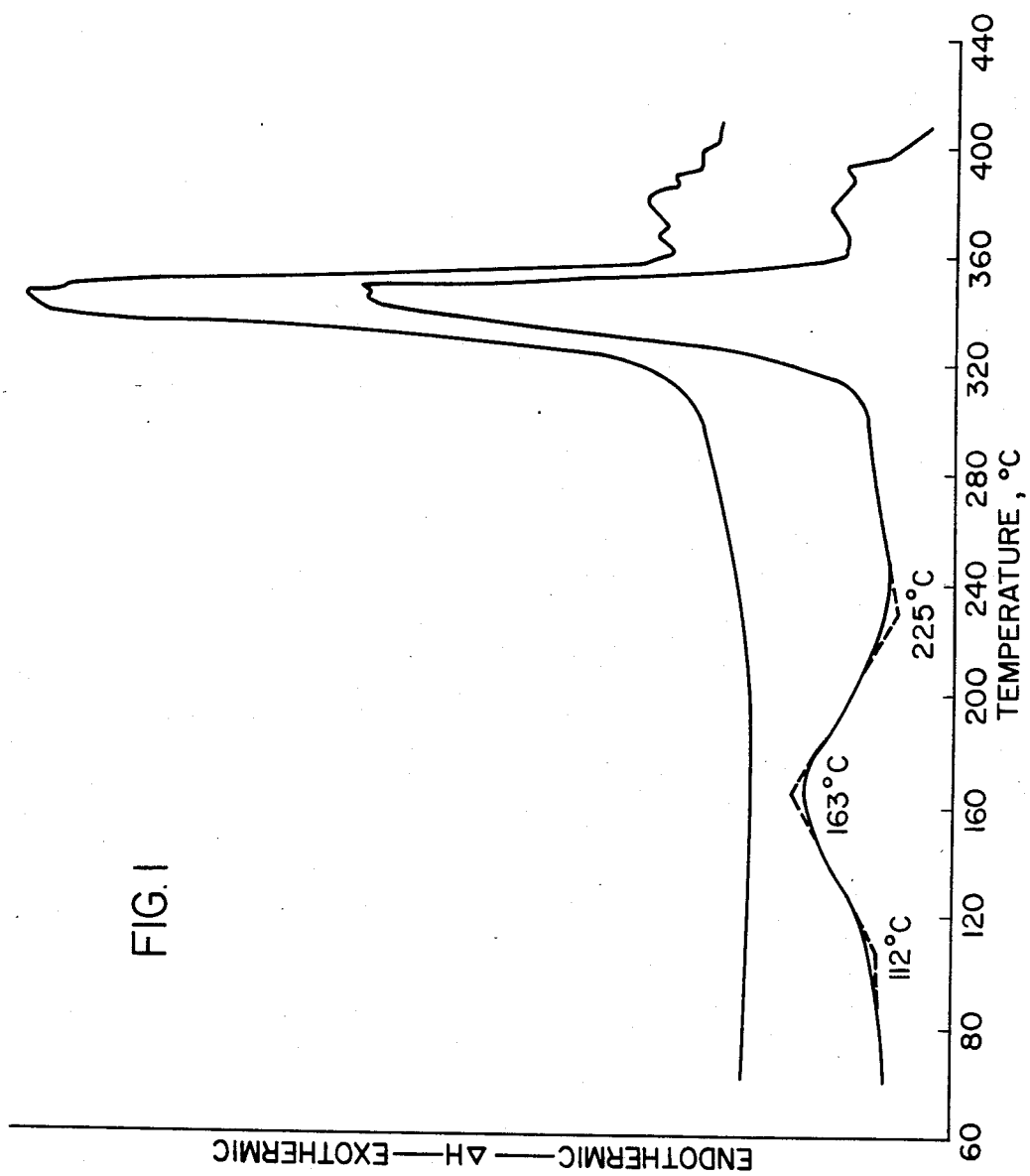

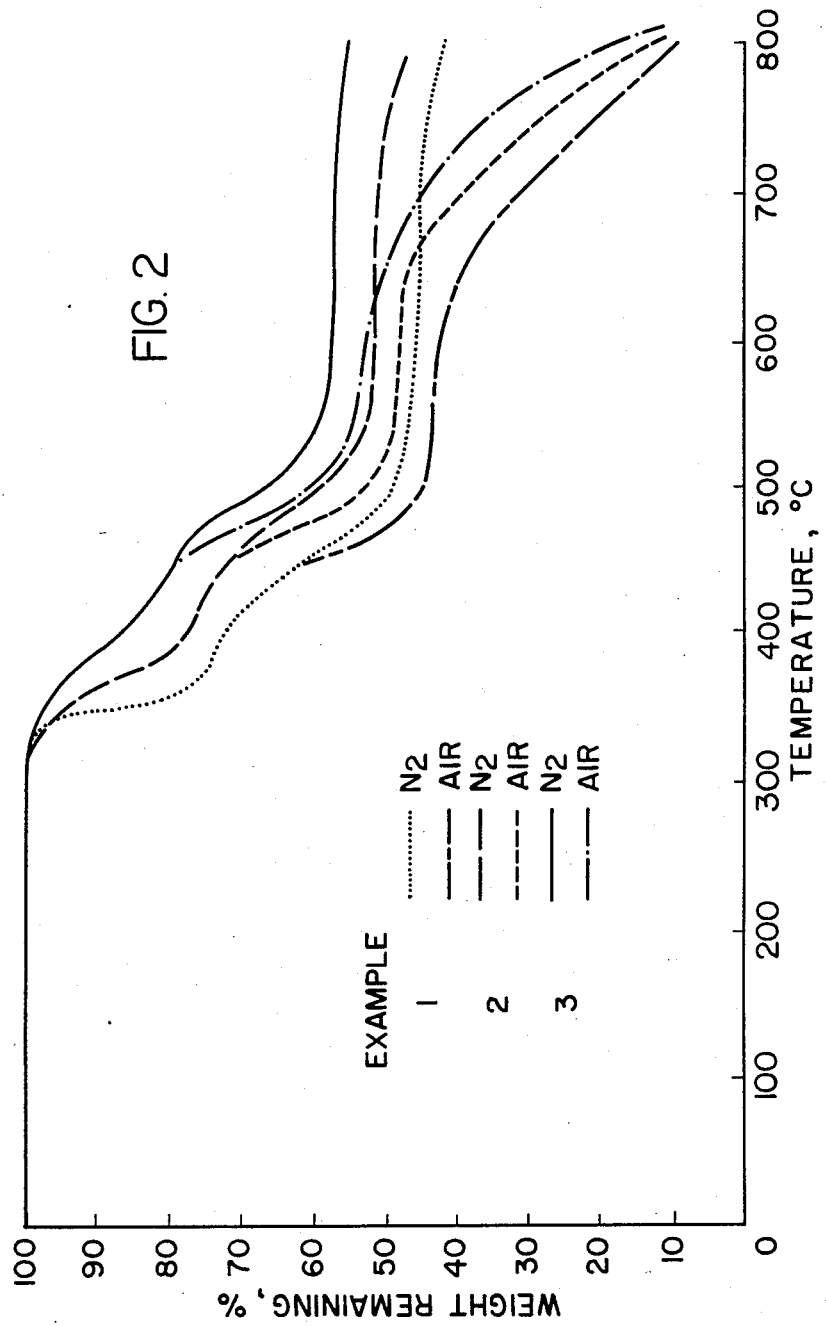

AMINOPHENOXYCYCLOTRIPHOSPHAZENE CURED EPOXY RESINS AND THE COMPOSITES, LAMINATES, ADHESIVES AND STRUCTURES THEREOF

ORIGIN OF THE INVENTION

The invention described herein was made in the performance of work under NASA contract and is subject to the provisions of Section 305 of the National Aeronautics and Space Act of 1958, Public Law 85-568 (72 Stat. 435; 42 USC 2457).

FIELD OF THE INVENTION

This invention relates to a process for curing epoxy resins with a phosphorus-containing curing agent, the cured resins which result and the composites, laminates, adhesives and structures produced from the cured resins.

BACKGROUND OF THE INVENTION

High performance, fiber-reinforced, organic matrix composites provide lightweight but strong structures. In such materials, the organic matrix is generally a thermosetting material. The most common thermosetting matrices used are the epoxies. The inherently flammable nature of many of the epoxies used, however, limits their widespread application for fire-resistant composites.

Cyclomatrix polyorganophosphazenes, which consist of a network of phosphazene rings coupled by multifunctional organic residues at the phosphorus atoms, provide heat- and fire-resistant polymer systems. Some aspects of the synthesis of organophosphazene-based multifunctional epoxies and their curing to polymers have been reported in the literature, such as in W. Bloom, U.S. Pat. No. 3,412,045 (1968); *Chem. Abstr.*, 70, 29723 (1969); H. Tsuchida, Kokai Tokkyo Koho 73,38687 (1973); *Chem. Abstr.* 81, 64307k (1974); Ya P. Belyayev and M. S. Trizno, *Plast. Massy*, 5, 77 (1974); *Chem. Abstr.*, 81 153388c (1974); Ya P. Belkyayev and M. S. Trizno, *Plast. Massy.* 8, 7 (1975); *Chem. Abstr.*, 83, 11241 (1975); H. Kawamura, Kokai Tokkyo Koho 73,37499 (1973); *Chem. Abstr.* 80, 15635 (1974); H. Kawamura, Kokai Tokkyo Koho 73,25758 (1973); *Chem. Abstr.*, 80, 109260 and 109261 (1974); M. Wajima, R. Tadas, and T. Nakamura, Kokai Tokkyo Koho, 73,76998 (1973); Chem. Abstr. 80, 109318 (1974); H. Maki, Kokai Tokkyo Koho 76,21000 (1976); *Chem. Abstr.*, 84, 165720 (1976); L. A. Alexeenko, V. V. Kireev, and D. F. Kupetov, *Plast. Massy,* 11, 13–14 (1978); *Chem. Abstr.*, 90, 104709 (1979); L. A. Alexeenko, U.S.S.R. Pat. 737412 (1980); *Chem. Abstr.*, 93, 133324 (1980); K. L. Paciorek, NASA-CR-165147-SN-8342-F; *Chem. Abstr.*, 94, 122476 (1981); and E. Devadoss, *J. Appl. Polym. Sci.*, 28, 921–941 (1983).

Other references of interest include *Macromolecules*, 16, 1250, (1983) and *J. Polymer Sci., Chem. Ed.*, 22, 927 (1984), as well as U.S. Pat. Nos. 4,316,006; 4,107,146; 4,124,557 and 4,405,738.

The polyorganophosphazene-epoxy systems obtained in most of these cases are based on products formed by mixing multifunctional reactants in which the amino or epoxy groups required for the reaction are not directly attached to the cyclotriphosphazene moiety. The resulting products are complex and usually thermally unstable.

STATEMENT OF THE INVENTION

It has now been found that epoxy resins can be thermally cured to tough, thermally stable, high char yield polymers usng aminophenoxycyclotriphosphazenes as curing agents. More specifically, the present invention relates to a process for preparing a thermally stable solid epoxy-aminophenoxycyclotriphosphazene polymer, and the process comprises: (a) combining an organic 1,2-epoxy resin having two or more 1,2-epoxy groups and a cyclotriphosphazene having from 2 to 6 aminophenoxy groups selected from bis(4-aminophenoxy)tetrakisphenoxycyclotriphosphazene; tris(4-aminophenoxy)-trisphenoxycyclotriphosphazene; tetrakis(4-aminophenoxy)-bisphenoxycyclotriphosphazene; pentakis(4-aminophenoxy)phenoxycyclotriphosphazene; or hexakis(4-aminophenoxy)cyclotriphosphazene; (b) heating the resulting mixture of step (a) at between about 110° and 135° C. for between about 2 and 15 min to dissolve the amine in the epoxy resin; (c) subsequently heating the mixture of step (b) at between about 165° and 195° C. for between about 0.5 and 10 hr to polymerize said mixture; and (d) postcuring the polymer of step (c) by heating at between about 215° and 235° C. for between about 0.25 and 2 hr. Reinforced moldings, composites, laminates, adhesives and structures formed from such materials have physical properties that are superior to equivalent epoxy resin systems not having the cyclotriphosphazene functional group.

The polymers, composites, laminates, adhesives, molded parts and the like are useful in aircraft and space craft applications where strength, light weight, elevated temperature stability and flame resistance are of importance. They are particularly useful in secondary structure applications in the cabin area of the aircraft. Further, solventless curing systems of the type described herein are preferred by industry to eliminate the formation of voids which are known to cause the deterioration of the mechanical properties of the cured matrix.

DETAILED DESCRIPTION OF THE INVENTION

The polymerization process of this invention and the resulting polymers employ certain phenoxycyclotriphosphazenes with p-amino groups substituted thereon numbering from two to six amine groups per molecule.

THE DI- OR POLYAMINES

In one embodiment the monomers used are di- or polyaminobenzene (or phenoxy) compounds, the preparation of which may begin with the reaction of hexachlorocyclotriphosphazene with a mixture of phenol and nitrophenol, and subsequently reducing the nitro groups to amino groups. The compounds may also be prepared by the reaction of the hexachlorocyclotriphosphazene with phenol and acetylaminophenol with subsequent hydrolysis of the acetyl group using either mild acid or base treatment to produce the amines.

In another embodiment hexachlorocyclotriphosphazene is treated with 4-nitrophenol in base to produce the hexanitrophenoxy compound which is reduced using platinum oxide and hydrogen to produce the hexakis(4-aminophenoxy)cyclotriphosphazene.

In another embodiment, the cyclic trimer hexachlorocyclotriphosphazene is first treated with sodium phenoxide which is then reacted in situ with sodium 4-nitrophenoxide in refluxing tetrahydrofuran to produce tris(4-nitrophenoxy)tris(phenoxy)cyclotrisphosphazene. After treatment using a reducing agent such as hydrogen and platinum oxide, the tris(4-aminophenoxy)-tris(phenoxy)cyclotriphosphazene is obtained.

In a further embodiment the aminocyclotriphosphazenes are made by acidic or basic hydrolysis of the acetylaminophenoxycyclotriphosphazenes made by reacting the triphenoxy trichlorocyclotriphosphazene or hexachlorocyclotriphosphazene with acetylaminophenol.

In another embodiment the hexachlorocyclotriphosphazene is reacted with sodium phenoxide and then with acetylaminophenoxide to produce the phenoxyacetylaminophenoxycyclotriphosphazene which is then hydrolyzed with either dilute acid, such as hydrochloric acid, HCl, or base, such as sodium hydroxide to produce the amino derivatives.

The present invention relates to the thermal curing of epoxy resins using aminophenoxycyclotriphosphazenes with or without solvent (neat) and includes any aminophenoxy, phenoxy cyclotriphosphazene where there are at least two amino groups per molecule. For instance, bis(4-aminophenoxy)-tetrakisphenoxy-, tetrakis(4-aminophenoxy)-bisphenoxy-, and pentakis(4-aminophenoxy)-phenoxy-cyclotriphosphazene are used with advantage in certain applications.

It is possible that mixtures of various ratios, from 90:10 to 10:90, of amine-containing cyclotriphosphazene monomers (e.g., tris(4-aminophenoxy)triphenoxycyclotriphosphazene and hexakis(4-aminophenoxy)cyclotriphosphazene) would be utilized in some applications.

EPOXY RESIN

The epoxy resins useful in this present invention include any epoxide having two or more 1,2-epoxy groups, preferably two to four 1,2-epoxy groups.

These epoxides include those di-, tri-, tetra-epoxides, etc. having an aromatic, aliphatic or a configuration of aromatic and aliphatic groups (z) separating the epoxides. Preferably, the number of aromatic groups are between 1 and 4. Preferred aromatic groups are phenyl and naphthyl. The aromatic groups may be further substituted with halogen atoms such as fluorine, chlorine or bromine to achieve desired properties. The number of aliphatic carbon atoms is preferably between 0 and 10. More preferably, the number of aliphatic atoms is between 1 and 4.

Useful commercial epoxides include, for example:

| Trade Name | Description/Supplier |
|---|---|
| EPON 825 | Diglycidylether of Bisphenol A/Shell Chemical Co./Houston, TX |
| DEN 438 | Polyglycidylether of Phenolformaldehyde novolac/Dow Chemical Co./Midland, MI |
| DER 542 | Diglycidylether of Tetrabromobisphenol A/Dow Chemical Co./Midland, MI |
| MY-720 | Tetraglycidylamine of bis(4-aminophenoxy)methane/Ciba-Geigy/Ardsley, NY |

The structures of these 1,2-epoxy resins are shown below:

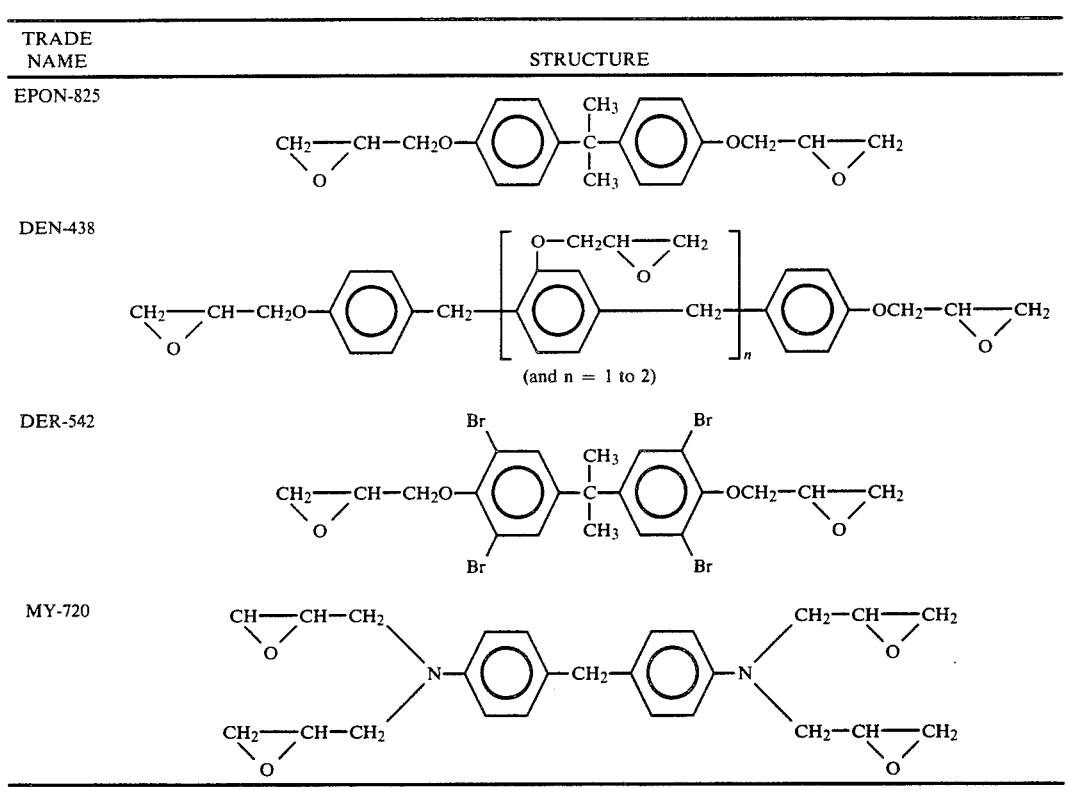

The epoxy resins within the present invention also include those described by S. Sherman et al. in "Epoxy Resins" in *Encyclopedia of Chemical Technology*, Vol. 9, pp. 267–290 (1980), which is incorporated herein by reference.

THE POLYMERIZATION AND THERMALLY STABLE POLYMERS

The di- or polyepoxides and the di- or polyamines have been described hereinabove.

The polymerization or curing of the monomers described herein is accomplished by combining a stoichiometrically equivalent mixture of the epoxy resin and the amine (1-epoxy group/1-amine hydrogen). The amine and epoxy monomers are usually combined at ambient temperature and pressure and thoroughly mixed, heated to between about 110° and 135° C., preferably between about 120° and 125° C. Usually the amine dissolves in the epoxide in a few minutes. The polymer is then cured with heating at about 170°-190° C., preferably between about 175° and 180° C. for between about 0.5 to 10 hr., preferably between about 2 to 3 hr. The polymer is finally cured at between about 220° to 230° C. for between about 0.1 and 2 hr., preferably about 0.5 hr. The time-temperature schedule used in each particular case depends on the size, configuration and amount of substrates (fillers, fibers, etc.) used. The preferred temperatures and time cited herein refer to small neat samples.

The general structure of the polymer for the epoxy resin and tris(4-aminophenoxy)-triphenoxycyclotriphosphazene adduct is shown below:

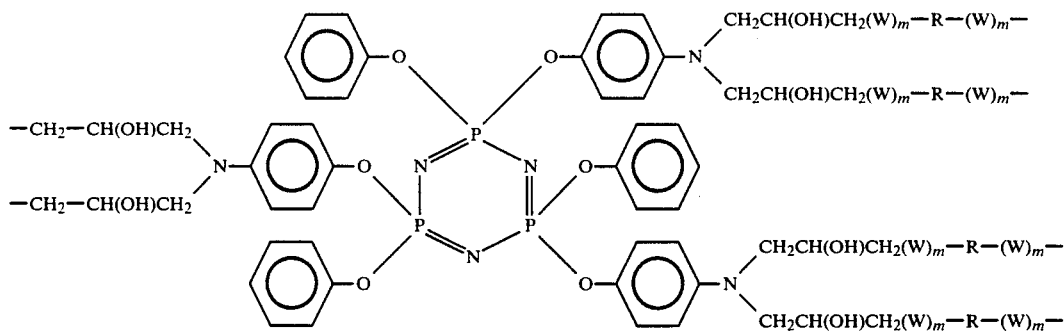

and for the epoxy resin and hexakis(4-aminophenoxy)-cyclotriphosphazene is:

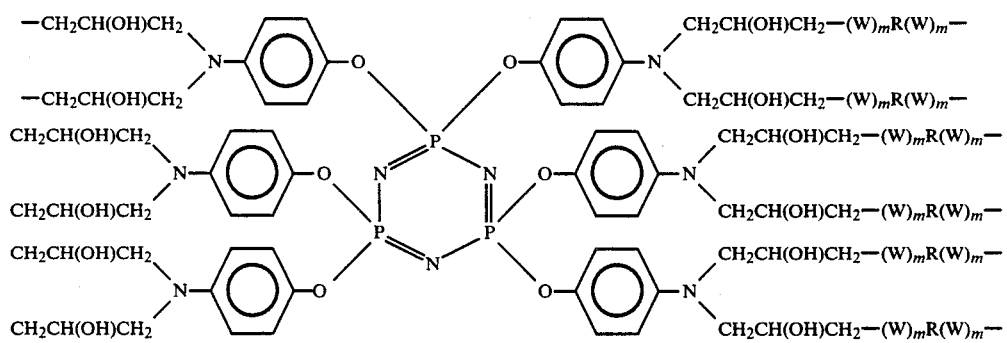

where R is diphenyldimethylmethane, [—φ—C(CH$_3$)$_2$—φ—]; diphenylmethane, [—φ—CH$_2$—φ—];, bis(dibromophenyl)dimethylmethane, [—φBr$_2$—C(CH$_3$)$_2$—φBr$_2$—]; or the novolac

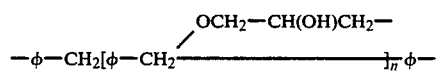

where n is between 1 and 2; W is a nitrogen or oxygen atom; and m is 1 when W is oxygen and m is 2 when W is nitrogen. Using the other cyclotriphosphazenes described herein, will produce similar polymer structures.

The cured polymer is very insoluble in solvents such as dimethylformamide, dimethylacetamide, methylene chloride (swells) and dimethylsulfoxide.

Preferably, the attachment of the phenyl groups in the structure of the epoxide moiety is at the 1,2- or 1,4-phenyl group positions. More preferably, the attachment is through the 1,4-positions. The term "φ" depicts a phenyl group which may be unsubstituted or mono- or polysubstituted at any positions.

The decomposition temperatures and char yields of the cured resins are described below in Table I.

FIG. 1 shows the differential scanning calorimeter thermograms for the uncured and cured resins in air. Exothermic peaks observed were analyzed for the onset temperature T$_{(os)}$ of the reaction obtained by the extrapolation of the positive slope side of the curve to base line, for the exothermic peak temperature T$_{(exo)}$ obtained by extrapolating the back side of the exothermic curves of the base line. Two exothermic peaks are observed in the uncured sample at 112°-225° C. and 320°-360° C. with the T$_{exo}$'s at 163° C. and 330° C. respectively. The exothermic peak with T$_{exo}$ at 163° C. indicates a polymerization whereas the T$_{exo}$ at 330° C. indicates mainly decomposition. The observation of T$_{os}$ at 112° C. for the first exothermic peak indicates that curing of DEN 438 with tris(4-aminophenoxy)-trisphenoxy-cyclotriphosphazene takes place at a comparatively lower temperature. This solventless curing at the lower temperature is much preferred in industry for producing composite structures, laminates and adhesives. In the cured resin the exothermic peak with T$_{exo}$ at 163° C. is absent, thus indicating the completion of the polymerization reaction between the amine and epoxy groups.

A similar DSC thermogram is obtained by curing of hexakis(4-aminophenoxy)-cyclotriphosphazene with epoxide resin DEN 438.

The thermogravimetric analysis (TGA) is performed using a DuPont 951 instrument coupled to a 1090 thermal analyzer. A heating rate of 10° C./min in used for air and nitrogen atmospheres. A flow rate of 100 ml$^3$/min of nitrogen is used. A differential scanning calorimeter DSC module with the DuPont 1090 thermal analyzer is used for the differential scanning calorimetric (DSC) analyses); 4–5 mg of a sample is used in an air atmosphere with a heating rate of 10° C./min.

Proton nuclear magnetic resonance ($^1$H-NMR) spectra are recorded on a Jeol 100 MHz-NMR spectrometer. The chemical shift ($\delta$) is given in parts per million with tetramethylsilane as the internal standard. Fourier-transform infrared (IR) spectra are recorded on a Nicolet FT-IR spectrophotometer using KBr pellets or NaCl disks.

The flexural properties of the composites are determined with an Instron tester using a span-to-depth ratio of 32:1 and a cross-head speed of 0.1 in./min. The ASTM D-790 procedure is followed; the sample is 0.5 in. wide. Tensile properties are determined using the ASTM D-638 procedure with a cross-head speed of 0.1 in./min.

Examples of the preparation of the polymers and articles thereof of this invention are provided below. These are presented to illustrate the invention, and are not to be construed as limiting its scope which is defined by the appended claims.

ing), 1624 (NH$_2$ bending), 1505 (aromatic), 1193, 1172 and 1161 (cyclotriphosphazene ring P=N), and 957, 880, 834 (NH wagging). For Preparation A and B also see Kumar et al., *Macromolecules*, Vol. 16, pp. 1250–1257, (1983) which is incorporated herein by reference.

PREPARATION C

Tris(4-nitrophenoxy)-trisphenoxycyclotriphosphazene (a) This material is obtained as a white solid by the treatment of sodium and phenol with hexachlorocyclotriphosphazene at −78° C. to produce the trichlorotriphenoxycyclotriphosphazene, according to D. Dell et al., *J. Chem. Soc.*, 4072 (1965), which is incorporated herein by reference. This material is further reacted with sodium 4-nitrophenoxide in refluxing tetrahydrofuran to give the title compound in good yield.

(b) Similarly proceeding as is described in Subpart (a) of this preparation, but using a ratio of 4 equivalents of phenol and 2 equivalents of sodium 4-nitrophenoxide (per 6 available chlorine atoms in hexachlorocyclotriphoshazene), there is obtained bis(4-nitrophenoxy)tetrakisphenoxycyclotriphosphazene in good yield.

(c) Similarly, proceeding as is described in Subpart (a) of this preparation, but using a ratio of 4 equivalents of sodium 4-nitrophenoxide and 2 equivalents of phenol (per 6 available chlorine atoms in hexachlorocyclotriphosphazene), there is obtained tetrakis(4-nitrophenox-

TABLE I

Decomposition Temperatures and Char Yields of Cured Resins

| | In N$_2$ | | | In air % | | | | |
|---|---|---|---|---|---|---|---|---|
| Example | PDT, °C. | PDT max, °C. (W$^a$)* | Char yield % 800° C. | PDT, °C. | PDT max, °C. (W$^a$) | Char Yield % 800° C. | 700° C. | 650° C. |
| 1 | 350 | 360(85) 450(59) | 42 | 350 | 360(85) 450(57) 725(25) | 12 | 32 | 39 |
| 2 | 340 | 365(86) 475(66) | 47 | 340 | 365(86) 475(59) 725(30) | 18 | 40 | 47 |
| 3 | 340 | 375 | 55 | 340 | 360(86) | 20 | 42 | 48 |
| DEN 438$^b$ (neat) | 266 | 428 | 31 | 266 | 610(0) | NIL | NIL | NIL |

*W$^a$ = weight of residue at indicated temperature.
$^b$DEN-438 is the epoxy in the neat uncured state and how it cures and decomposes with heat. The polymer has essentially no char yield at 650, 700 or 800° C.
PDT = Polymer Decomposition Temperature

PREPARATION A

Hexakis(4-nitrophenoxy)-cyclotriphosphazene

This material is prepared according to the method of Kober et al., *Inorganic Chemistry*, Vol. 5, p. 2239 (1966), which is incorporated herein by reference, by treatment of hexachlorocyclotriphosphazene with p-nitrophenol and potassium hydroxide. Hexakis(4-nitrophenoxy)-cyclotriphosphazene having a melting point of 261°–264° C. is obtained (lit. m.p. 264° C.). The infrared spectrum (in KBr), (cm$^{-1}$) is 1589 (aromatic), 1522 and 1348 (asymmetrical and symmetrical nitro group stretching) and 1203, 1182 and 1163 (cyclotriphosphazene P=N).

PREPARATION B

Hexakis(4-aminophenoxy)cyclotriphosphazene

The reduction of the compound of Preparation A with hydrogen and aniline solution produces the title compound as described by Allcock et al., *Chem. Eng. News*, Apr. 22, 1968, pp. 68–81. The infrared spectrum (in KBr), (cm$^{-1}$) is 3419, 3371 and 3354 (NH$_2$ stretchy)bisphenoxycyclotriphosphazene in good yield.

(d) Similarly proceeding as is described in Subpart (a) of this preparation but using a mixture of 1 equivalent of phenol and 5 equivalents of sodium 4-nitrophenoxide (per 6 available chlorine atoms in hexachlorocyclotriphosphazene), there is obtained the corresponding pentakis(4-nitrophenoxy)phenoxycyclotriphosphazene in good yield.

PREPARATION D

Tris(4-aminophenoxy)-tris(phenoxy)cyclotriphosphazene (a) The compound of Preparation C is reduced with molecular hydrogen in the presence of PtO$_2$ as catalyst to yield the title compound in good yield. The structure is confirmed by infrared and proton nuclear magnetic resonance spectroscopy. Also, see Kumar et al., *J. Polymer Science: Polymer Chem. Ed.*, Vol. 22, 927–943 (1984) which is incorporated herein by reference.

(b) Similarly proceeding as is described in Subpart (a) of this preparation using sufficient PtO$_2$ and hydrogen and using the substituted triphosphazene of Preparation C, Subpart (b); Subpart (c) and Subpart (d), there is obtained the corresponding bis(4-aminophenoxy)tetrakisphenoxycyclotriphosphazene; tetrakis(4-aminophenoxy)bisphenoxycyclotriphosphazene; and pentakis(4-aminophenoxy)phenoxycyclotriphosphazene, respectively.

EXAMPLE 1

Polymer of Epoxy Resin DEN 438 and Tris(4-aminophenoxy)trisphenoxycyclotriphosphazene A stoichiometric mixture (1 epoxy group to 1-amine hydrogen) of epoxy resin DEN 438 having an epoxy equivalent weight of 176 to 181 (10.0 g) and tris(4-aminophenoxy)triphenoxycyclotriphosphazene (7.40 g) is prepared by thorough mixing at ambient temperature and pressure FIG. 1, Uncured Resin 1). The amine dissolves into the epoxy resin within 5 minutes when heated at 120° to 125° C. The polymer is then cured in an aluminum cup placed in an oven maintained at 175° to 180° C. for 2.5 hrs. The curing temperature is then raised to 225° C. for 0.5 hrs. The curing reaction is monitored by infrared and differential scanning calorimetry. A tough brown cured resin is obtained (FIG. 1, Cured Resin 2). The cured resin is clear indicating that the mixture does not undergo phase separation during the polymerization.

EXAMPLE 2

Polymer of Epoxy Resin DEN 438 and Tris(4-aminophenoxy)-trisphenoxycyclotriphosphazene A stoichiometric mixture (1-epoxy group to 1-amine hydrogen) of epoxy resin DEN 438 (1.25 g) and tris(4-aminophenoxy)trisphenoxycyclotriphosphazene (1.85 g) is prepared according to the reaction conditions described in Example 1. A tough brown clear cured resin is obtained.

EXAMPLE 3

Polymer of Epoxy Resin DEN 438 and Hexakis-(4-aminophenoxy)-cyclotriphosphazene

A stoichiometric mixture (1-epoxy group to 1-amine hydrogen) of epoxy resin DEN 438 (1.78 g) and hexakis-(4-aminophenoxy)-cyclotriphosphazene (1.74 g) are mixed and heated in a manner similar to that described in Example 1. The obtained cured resin is tough, brown, and clear.

Although in these three examples no solvent is used, solvents such as methylethyl ketone, acetone, tetrahydrofuran, dioxan, DMF, DMAC, dimethylsulfoxide (DMSO) are useful for making solutions of amine and epoxy resins to facilitate the coating of fabrics or other substrates and casting of films.

EXAMPLE 4

Composite Fabrication (a) Test laminates are prepared by coating graphite cloth (Hercules Magnamite Graphite cloth type AS, W sizing; Magna, Utah) with a dimethylacetamide solution (40%) of the formulation of Example 1, and drying the coated cloth (prepregs) in an oven at 105°–110° C. for 5 to 10 min. The prepregs are then stacked and pressed between aluminum plates covered with aluminum foil in a press held at 180° C. for 2.5 hr. The temperature of the press is then raised to 225° C. for 30 min. The pressure maintained on the layers is about 50–70 psi. A tough fire-resistant composite laminated structure is obtained.

(b) In a similar manner, the laminate of Subpart (a) above is prepared without solvent. The formulation of Example 1 is spread over the Graphite cloth using mild heat and pressure. Laminates having comparable physical properties are obtained.

The resin component of the laminate is determined by boiling with concentrated nitric acid. Table II shows the results of the physical tests done on the graphite laminate. For comparison, a graphite laminate made using Ciba-Geigy epoxy resin MY-720 tetraglycidylamine of 4,4'-diaminodiphenylmethane which is cured using 4,4'-diaminodiphenylsulfone (DDS). The values shown in Table II definitely show that the cured resin and laminate is superior to the commonly used epoxy system. The 55% LOI determined on these laminates suggests that they can be used in fire-resistant and in elevated temperature applications.

TABLE II

| Physical Properties of Graphite Cloth Laminates | | | |
| --- | --- | --- | --- |
| Property Tested | Test Method | Epoxy Example 1 | Epoxy[a] |
| Resin content (%) | | 34 | 25 |
| Density (g/cm$^3$) | | 1.34 | 1.57 |
| Flammability | | Non-burning | Non-burning |
| LOI (% O$_2$) | ASTM D-2863 | 55 | 45 |
| Tensile Strength (psi) | | 72,080 | 51,639 |
| (MN/m$^2$) | ASTM D-638 | 497 | 356 |
| Flexural Strength (psi) | | 105,480 | 79,808 |
| (MN/m$^2$) | ASTM D-790 | 727 | 550 |
| Short Beam Shear (psi) | | 5,636 | 7,749 |
| (MN/m$^2$) | ASTM D-2344 | 38.76 | 53.42 |

[a]Ciba-Geigy epoxy resin MY-720 (tetraglycidylamine of 4,4'-diaminodiphenylmethane) cured with 4,4'-diaminodiphenylsulfone (DDS).

The dynamic thermographic curve for the cured samples, of Examples 1, 2 and 3 in nitrogen and in air are shown in FIG. 2. All three cured resins show a similar pattern of decomposition. In nitrogen, a two-step decomposition is observed wherein in air a three-step decomposition is observed. Both in air and in nitrogen, the onset of decomposition ranges from 340°–350° C. A faster weight loss is observed in air above 650° C. The high char yield of these cured resins, particularly in air atmosphere, to 680°–700° C. gives these systems desirable properties for fire and heat resistant applications. The high char yield indicates good retention of structural integrity to elevated temperatures.

Additional fibrous materials which are useful in the present invention to produce useful composites and laminates include glass fiber, silicon nitride, silicon carbide, boronnitride and the like.

While the present invention has been described with reference to specific embodiments thereof, it will be understood by those skilled in this art that various changes may be made and that equivalent steps may be substituted without departing from the true spirit and scope of the present invention. All such modifications or changes are intended to be included within the scope of the following claims.

We claim:

1. A process for preparing a thermally stable solid epoxy-aminophenoxycyclotriphosphazene polymer, which process comprises:
(a) combining an organic 1,2-epoxy resin having two or more 1,2-epoxy groups and an amino containing cyclotriphosphazene derivative selected from bis(4-aminophenoxy)tetrakisphenoxycyclotriphosazene, tris(4-aminophenoxy)-trisphenoxycyclotriphosphazene, tetrakis(4-aminophenoxy)bisphenoxycyclotriphosphazene, pentakis(4-aminophenoxy)phenoxycyclotriphosphazene, or hexakis(4-aminophenoxy)cyclotriphosphazene;

(b) heating the resulting mixture of step (a) at between about 110° and 135° C. for between about 2 and 10 min;

(c) subsequently heating the product of step (b) at between about 165° and 190° C. for between about 0.5 and 10 hr; and (d) heating the polymer of step (c) at between about 215° and 235° C. for between about 0.1 and 2 hr.

2. The process of claim 1 wherein in step (a) the organic 1,2-epoxy resin has the formula:

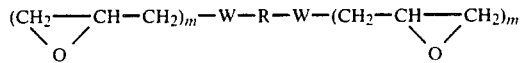

wherein

R is diphenyldimethylmethane, diphenylmethane, bis(dibromophenyl)dimethylmethane, or a phenol-formaldehyde novolac

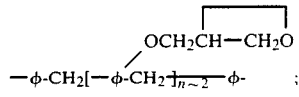

W is a nitrogen or oxygen atom;

m is 1 when W is oxygen, m is 2 when W is nitrogen and n is between or equal to 1 and 2.

3. The process of claim 2 wherein in step (a) the cyclotriphosphazene is tris-(4-aminophenoxy)-trisphenoxycyclotriphosphazene.

4. The process of claim 3 wherein in step (a) in the epoxy resin,
R is diphenyldimethylmethane; and
W is oxygen.

5. The process of claim 2 wherein in step (a) the cyclotriphosphazene is hexakis(4-aminophenoxy)-cyclotriphosphazene.

6. The process of claim 5 wherein in step (a) in the epoxy resin,
R is diphenyldimethylmethane; and
W is oxygen.

7. The process of claim 3 wherein in step (b) the mixture is first heated at between 120° to 125° C.; in step (c) the curing is accomplished by heating at 175° to 180° C.; and in step (d) the polymer is further cured at about 225° C.

8. The process of claim 5 wherein in step (b) the mixture is first heated between 120° and 125° C., in step (c) the polymer is heated at 175° to 180° C.; and in step (d) the polymer is cured at about 225° C.

9. The process of claim 3 wherein the epoxy resin is the polyglycidylether of a phenolformaldehyde novolac.

10. A thermally stable solid epoxy aminophenoxycyclotriphosphazene polymer formed by the thermal polymerization of an epoxy resin having the formula:

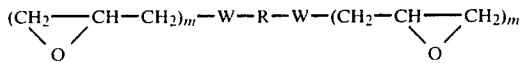

wherein R is diphenyldimethylmethane, diphenylmethane, bis(dibromophenyl)dimethylmethane, or phenol-formaldehyde novolac

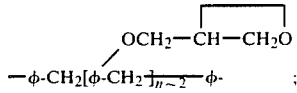

W is a nitrogen or oxygen;

m is 1 when W is oxygen, m is 2 when W is nitrogen and n is between or equal to 1 and 2; and an amino phenoxycyclotriphosphazene selected from bis(4-aminophenoxy)tetrakisphenoxycyclotriphosphazene, tris(4-aminophenoxy)-trisphenoxycyclotriphosphazene, tetrakis(4-aminophenoxy)bisphenoxycyclotriphosphazene, pentakis(4-aminophenoxy)phenoxycyclotriphosphazene, and hexakis(4-aminophenoxy)cyclotriphosphazene.

11. The polymer of claim 10 wherein the phenoxycyclotriphosphazene is hexakis(4-aminophenoxy)-cyclophosphazene.

12. The polymer of claim 11 wherein in the epoxy resin R is diphenyldimethylmethane and W is oxygen.

13. The polymer of claim 11 wherein in the epoxy resin R is

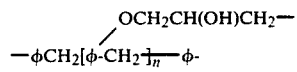

where n is equal to or between 1 and 2 and W is oxygen.

14. The polymer of claim 10 wherein the phenoxycyclotriphosphazene is tris(4-aminophenoxy)tris phenoxycyclotriphosphazene.

15. The polymer of claim 14 wherein in the epoxy resin, W is oxygen and R is diphenyldimethylmethane.

16. The polymer of claim 14 wherein in the epoxy resin R is

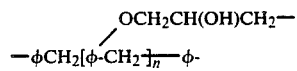

where n is between or equal to 1 and 2 and W is oxygen.

17. A fire-resistant and elevated temperature composite comprising the polymer of claim 10 and a material suitable for forming a composite.

18. A fire-resistant and elevated temperature stable laminate comprising the polymer of claim 10 and a fiberous material suitable for forming a laminate.

19. A fire-resistant and elevated temperature stable composite comprising the polymer of claim 11 and a material suitable for forming a composite.

20. A fire-resistant and elevated temperature stable laminate comprising the polymer of claim 14 and a fibrous material suitable for forming a laminate.

* * * * *